United States Patent [19]
Fairfax et al.

[11] Patent Number: 5,634,471
[45] Date of Patent: Jun. 3, 1997

[54] FLOWMETERS

[75] Inventors: Andrew J. Fairfax, Penn House; David J. Hitchings, Stone, both of England

[73] Assignee: British Technology Group Limited, London, England

[21] Appl. No.: 379,662

[22] PCT Filed: Sep. 8, 1993

[86] PCT No.: PCT/GB93/01899

§ 371 Date: Feb. 9, 1995

§ 102(e) Date: Feb. 9, 1995

[87] PCT Pub. No.: WO94/05204

PCT Pub. Date: Mar. 17, 1994

[30] Foreign Application Priority Data

Sep. 9, 1992 [GB] United Kingdom ............ 9219102

[51] Int. Cl.$^6$ ............................................. A61B 5/08
[52] U.S. Cl. ...................................................... 128/725
[58] Field of Search ............................. 128/716, 725, 128/726, 727, 728, 730

[56] References Cited

U.S. PATENT DOCUMENTS

| 4,489,754 | 12/1984 | Seessle et al. |
| 4,509,551 | 4/1985 | Luper. |
| 4,736,750 | 4/1988 | Valdespino et al. |
| 4,768,520 | 9/1988 | Varraux et al. ............ 128/725 |
| 5,058,601 | 10/1991 | Riker ............ 128/725 |
| 5,224,487 | 7/1993 | Bellofatto et al. ............ 128/716 |
| 5,246,010 | 9/1993 | Gazzara et al. ............ 128/725 |
| 5,277,195 | 1/1994 | Williams ............ 128/725 |
| 5,501,231 | 3/1996 | Kaish ............ 128/725 |
| 5,518,002 | 5/1996 | Wolf et al. ............ 128/725 |

FOREIGN PATENT DOCUMENTS

| 0 025 576 | 3/1981 | European Pat. Off. |
| 0045388 | 7/1981 | European Pat. Off. |
| 0 314 325 | 5/1989 | European Pat. Off. |
| 0 373 886 | 6/1990 | European Pat. Off. |
| 239 665 | 10/1986 | Germany. |
| 2 238 389 | 5/1991 | United Kingdom. |

Primary Examiner—Lee S. Cohen
Assistant Examiner—Eric F. Winakur
Attorney, Agent, or Firm—Nixon & Vanderhye

[57] ABSTRACT

Peak expiratory flow meter for measuring the expiratory flow rate of a subject having a flow inhibitory device normally effective to inhibit expiratory flow through the peak expiratory flow meter, the flow inhibitory device being operable in response to attainment of a predetermined expiratory pressure to allow the expiratory flow. From the PEF measured, the airway passage resistance can be determined. Further lung characteristics can be determined from the shape of the decay portion or the expiratory flow curve. The meter has clinical application in the monitoring and diagnosis of asthma and other pulmonary diseases.

18 Claims, 1 Drawing Sheet ns and are open to
FLOWMETERS

This invention concerns flowmeters and, more particularly, such meters for measuring peak expiratory flow, commonly denoted as PEF.

BACKGROUND OF THE INVENTION

PEF meters are now seen to be of clinical value in the diagnosis and management of asthma and they are widely prescribed for this purpose in a portable form suited to domiciliary usage. This last form typically involves a piston-and-cylinder assembly through which the piston is movable against a spring bias by the action of a forced expiration, with the piston position affording a measure of the expiratory flow. A well known meter of this form is described in UK Patent Specification No. 1,463,814.

In any event, notwithstanding the value and usage of PEF meters, work leading to development of the present invention indicates that they have shortcomings and are open to improvement. More specifically their operation is effort-dependent. As a consequence of this, successive measures taken over a period of time by the same subject are not necessarily usefully comparable, and comparability between measures taken from different patients is probably less reliable.

SUMMARY OF THE INVENTION

An object of the present invention is to improve this situation and, to this end, it is proposed that a PEF meter be provided with means normally effective to inhibit expiratory flow through the meter, such means being operable in response to attainment of a predetermined expiratory pressure to allow the expiratory flow.

In a preferred form the flow inhibiting means of the invention comprises a valve mechanism which normally closes the expiratory flow path through the meter, the mechanism being operable to open the path.

The flow inhibiting means is preferably of a fast acting form when operated, in the sense that its operation takes a short time relative to the duration of a forced expiration and does not take significantly longer than attainment of peak flow during such expiration.

Preferably the flow inhibiting means is adapted to operate in a time significantly shorter than that taken for attainment of peak flow during forced expiration.

For these last purposes, the flow inhibiting means suitably comprises a shutter or flap valve mechanism operable to open in response to an electrical signal from a pressure detector. Such a mechanism will provide a fast-acting flow inhibiting means of minimal resistance when open.

In an alternative arrangement, the flow inhibiting means comprises a mechanism of a mechanical or magnetic form operable to open in direct response to the relevant pressure.

The meter will of course comprise some means for measuring the expiratory flow after the operation of the flow inhibiting means. This flow measuring means preferably provides an electrical signal representation of the measured flow, and for this purpose, a flow transducer of hot wire anemometer form is appropriate.

Given the signal output from such a transducer, it is a simple matter to display and/or record the flow through the expiration, or just the peak value attained during expiration.

The predetermined expiratory pressure is preferably a pressure value preset for the meter. This value may or may not be adjusted from one measure to the next or from one subject to the next.

The invention also envisages a pressure threshold whose value is not preset for the meter, but decided automatically during use. To this end the meter is provided with computing means to decide the value of the predetermined pressure in response to the electrical signal.

In this way the pressure threshold at which the flow inhibiting means operates is predetermined in the sense that, although its value is not preset, the manner in which it is determined is prescribed.

In a preferred form, a release pressure value for the flow inhibiting means is preset, and the computing means is programmed to open the flow inhibiting means at a pressure level lower than this release pressure value if such a pressure level is maintained for a predetermined length of time.

In another aspect of the invention, a method of measuring pulmonary function in a subject is provided, said method comprising:

providing a flow meter having a means normally effective to inhibit expiratory flow through the meter;

having the subject attempt expiratory flow through the meter;

automatically operating the flow inhibiting means on attainment of a predetermined pressure to allow flow through the meter, such that the subject is induced to produce peak expiratory flow; and measuring the expiratory flow through the meter.

The basis of the invention is that the provision of a pressure threshold, which must be overcome by the forced expiration before flow and measurement can occur, will be such that the subject under test cannot readily control the process but, on the contrary, is induced to produce a maximal flow and so render the process effort-independent. It is preferable for this purpose that the pressure threshold be adjustable to suit the individual capabilities of different subjects, but retention of the same threshold for a given subject renders successive measurement results directly comparable and results from different subjects using different thresholds are, it will be appreciated, also comparable. Whether the threshold expiratory pressure is fixed from subject to subject, or set for a particular individual, its value will in any case be significantly higher than the minimum perceptible breath pressure, otherwise it will not be possible to induce maximal expiratory flow. It is thought that the minimum threshold appropriate for this purpose will be about 0.5 $kN_m^{-2}$, equivalent to about 5 cm $H_2O$. For relatively healthy, adult subjects, an appropriate predetermined expiratory pressure is likely to be between about 10 and 20 $kN_m^{-2}$ (approximately 100–200 cm $H_2O$).

In the form of the invention wherein the pressure threshold is not a preset valve for the meter, but is decided automatically during the use of the meter, the pressure level at which the flow inhibiting means operates will still be high enough to induce maximal expiratory flow from the subject.

In these effort-independent circumstances the peak flow is theoretically proportional to the flow release pressure and inversely proportional to the airways resistance of the subject, the resistance of the meter itself typically being sufficiently small in comparison that it can effectively be ignored. Moreover, if the expiratory flow measured is plotted against time there is seen to be a fast rise up to the peak flow followed by a relatively long decay of variable form determined by the physical properties of the lungs such as resistance and compliance. It is to be noted that these last parameters are considered to change in value together with lung deflation and different mathematical models have been proposed to represent this situation. However, there is no reason to suppose that a meter according to the invention cannot be provided with a computational facility dedicated to determination of further parameters on the basis of a chosen model, or record the flow data for further analysis.

The meter of the present invention can be used in the diagnosis and monitoring of asthma and other pulmonary diseases and obstructive airway conditions. It is also suitable for use as a laboratory instrument for measuring pulmonary function or, more specifically, pulmonary mechanical parameters, in all subjects, for example as part of a health screening programme.

BRIEF DESCRIPTION OF THE DRAWINGS

An embodiment of the invention will now be described by way of example with reference to the accompanying drawings, in which.

DETAILED DESCRIPTION OF PREFERRED EMBODIMENTS

Figure 1:
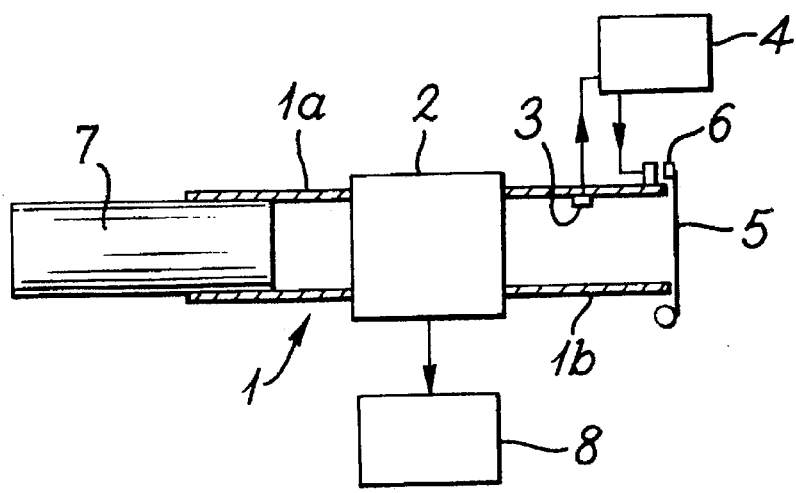
FIG. 1 illustrates a flowmeter according to the invention.

The instrument shown in FIG. 1 is a PEF meter according to the present invention. It consists of flow passage means which is represented in FIG. 1 as a tubular body 1 with an upstream portion 1a and a downstream portion 1b, between which a flow transducer 2 for measuring a patient's expiratory flowrate is arranged. The transducer should provide an accurate measure of total flowrate across the cross section of the air passage while providing negligible resistance to flow and a sufficiently high frequency response. It has been found that a spiral hot wire anemometer such as that produced by Dantec Measuring Technology is appropriate for this application.

In the downstream portion 1b of the meter a pressure transducer 3 is located, which provides a signal able by way of a control 4 to release an electromagnetic latch 6 on attainment of a predetermined pressure. At the downstream end of the meter a quick acting flow inhibiting means is provided, which is represented in FIG. 1 as an external flap valve (a so-called face valve) 5 retained by electromagnetic latch 6. Other types of valve which are capable of operating sufficiently rapidly to open completely are suitable for this purpose. Valve 5 is preferably sealed when closed against the annular end of the downstream portion 1b of the meter by means of a rubber O-ring, in order to prevent leakage past the valve. The pivot point for the face valve is arranged such that the valve drops away from the O-ring seal under the force of gravity without any danger of sliding contact with it. Additionally, a spring means may be incorporated in the valve to accelerate the opening operation.

A disposable mouthpiece 7 is provided in the upstream end of the meter. The mouthpiece can be discarded after each use of the instrument to avoid the possibility of contamination from one test to the next. Alternatively the mouthpiece may be reusable, preferably sterilised between uses.

The flow transducer 2 is connected to a display/record means 8. This can be programmed not only to display and store the patient's expiratory flow record, but also to alert the patient as to when to carry out the test, to set the release pressure as and if appropriate for the patient, to direct him/her as to what medication to take, and to automatically record data such as clocktime, date, etc. An automated meter/recorder of this type will thus avoid the need for the asthma patient to keep a record of his/her test data and this will in turn encourage the use of self-monitoring.

The operation of the meter is largely self evident from the above description. Valve 5 is closed and latched and, with a fresh mouthpiece 7, the subject attempts a forced expiration through the meter. This builds up a back-pressure within the instrument, and when this pressure reaches a predetermined threshold level as set by control 4 the latch 6 operates and the valve 5 quickly drops away. The resulting expiratory flow through the meter—effectively effort-independent as explained previously—is measured with flow transducer 2 and can be displayed and recorded.

A modification and simplification of the design of FIG. 1 is envisaged, wherein the pressure transducer 3, control 4 and electromagnetic latch 6 are replaced by a simple magnetic latch acting to hold valve 5 closed. The back-pressure in the meter will exert a force on the valve equal to the pressure multiplied by the valve face area. The opening of the valve will therefore be triggered when the force on the latch overcomes the fixed magnetic attraction force between the latch components, in other words, in direct response to the obtainment of the relevant pressure. The release pressure can be predetermined by altering the overlap between the two components of the magnetic latch, decreasing the area of overlap to decrease the release pressure at which the valve opens. Alternatively, a mechanical latch, such as a detent set to release under a preset load, may be used. Again, this operates in direct response to the obtainment of the relevant pressure.

Figure 2:
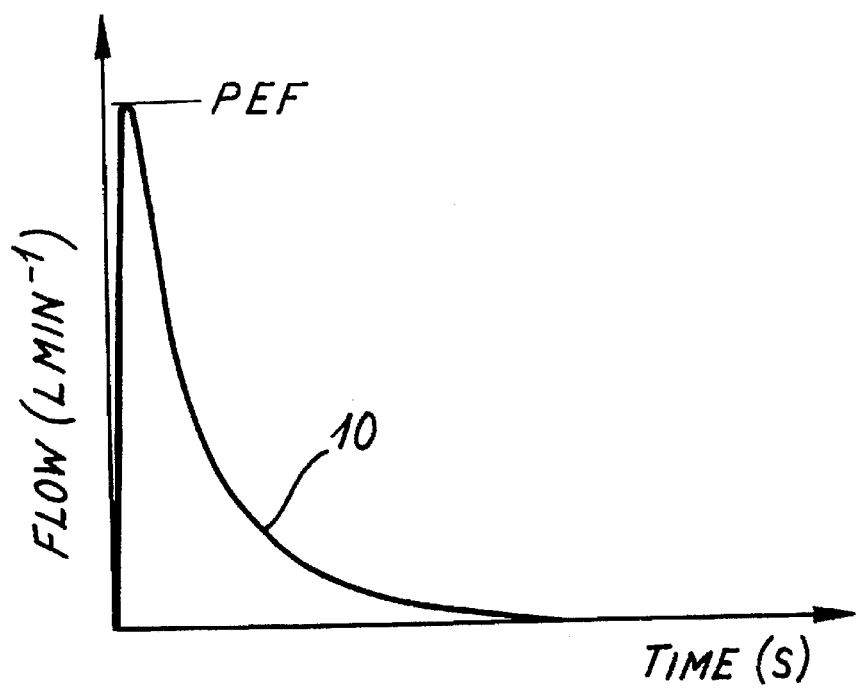
FIG. 2 shows a flowrate-time plot from a flow transducer in the meter of FIG. 1.

FIG. 2 illustrates a typical output plot from flow transducer 2. As explained above, with a predetermined release pressure the peak expiratory flow PEF is inversely proportional to the resistance in series with the instrument. The lung resistance can therefore be determined from calibration of the PEF of the expiration test. Moreover, the shape of the decay curve 10 provides important information as to the properties of the lung airways, and is determined by the complex impedance of the lungs and other physiological and anatomical factors. In a simple model the lung may be modelled as an RC (resistor-capacitor) electrical analogue circuit, where lung flow resistance is represented by R and lung compliance by C. The expiratory flowrate-time curve is then represented by the current-time curve of the circuit as the capacitor discharges through the resistor, where $I=I_0 e^{-t/RC}$. The shape of the curve can therefore be used to determine an RC value for the lung, and since R can be determined as described above from the PEF value, C can be calculated. Many more complex models exist for the lung, but it is thought that using this very simple analogue, very significant clinical information can be determined.

The invention has been described in the context of a particular embodiment. However, it is to be understood that it is not limited thereto and other forms of instrument are equally possible. For example, the fast acting valve may be placed upstream of the flow transducer.

The pressure threshold at which valve 5 opens need not necessarily be preset for the meter, but can be decided automatically in a prescribed manner during use as the subject attempts expiratory flow. In particular, a pressure threshold may be preset for the meter, but in the case that the subject is unable to attain such an expiratory pressure the meter may be programmed such that when a peak pressure level lower than this preset pressure is reached and maintained for a predetermined length of time—say 200 ms—then the valve will automatically operate. The resulting expiratory flow is likely still to show a useful PEF value, especially if the triggering pressure is only marginally below the preset pressure value.

We claim:

1. A peak expiratory flow meter for determining the expiratory flow rate of a subject, comprising:

flow passage means for transporting expiratory flow along an expiratory flow passage, said flow passage means having a first end for receiving expiratory air from said subject and a second end through which expiratory flow exits to the environment; and flow inhibition means connected to said flow passage means normally effective to inhibit expiratory flow through said flow passage means, said flow inhibition means comprising a valve mechanism which normally closes said expiratory flow passage, said valve mechanism opening completely and in a short time relative to the duration of forced expiration from said subject in response to attainment of a predetermined expiratory pressure to allow expiratory flow through said flow passage means and out through said second end to the environment.

2. A meter according to claim 1 wherein operation of said flow inhibition means does not take significantly longer than attainment of peak flow during a forced expiration of said subject.

3. A meter according to claim 2 wherein the flow inhibition means operates in a time significantly shorter than that taken for attainment of peak flow during forced expiration.

4. A meter according to claim 2 wherein said flow inhibition means comprises a shutter or flap valve mechanism which opens in response to an electrical signal from a pressure detector.

5. A meter according to claim 4, wherein computing means is provided for determining a value of said predetermined pressure in response to said electrical signal.

6. A meter according to claim 5, wherein a release pressure value for said flow inhibition means is preset and said computing means is programmed to provide a signal which opens said inhibition flow means at a pressure level lower than a release pressure value if said pressure level is maintained for a predetermined length of time.

7. A meter according to claim 2, wherein said flow inhibition means comprises a mechanical or magnetic mechanism which opens in direct response to said predetermined expiratory pressure.

8. A meter according to claim 1, wherein said predetermined expiratory pressure is a pressure value preset for the meter.

9. A meter according to claim 9, and further including a flow measuring means for providing an electrical signal representation of expiratory flow through passage.

10. A meter according to claim 9, wherein said flow measuring means is a hot wire anemometer flow transducer.

11. A meter according to claim 1, further including flow data display and/or recording means.

12. A peak expiratory flow meter according to claim 1, wherein said predetermined expiratory pressure is about 0.5 $kN_m^{-2}$.

13. A peak expiratory flow meter according to claim 1, wherein said predetermined expiratory pressure is about 10 to 20 $kN_m^{-2}$.

14. A method of measuring pulmonary function in a subject, said method comprising:

providing a flow meter having an expiratory flow passage means for transporting expiratory flow along an expiratory flow passage, said flow passage means having a first end for receiving expiratory air from a subject and a second end through which expiratory flow exits to the environment and flow inhibition means normally effective to inhibit expiratory flow through said flow passage means, wherein said flow inhibition means comprises a valve mechanism which normally closes said expiratory flow passage, said valve mechanism opening completely and in a short time relative to the duration of forced expiration from the subject in response to attainment of a predetermined expiratory pressure to allow expiratory flow through said flow passage means and out through said second end to the environment;

having the subject to attempt expiratory flow through the meter;

automatically operating said valve mechanism on attainment of a predetermined expiratory pressure to allow expiratory flow through the flow passage means, such that the subject is induced to produce a peak expiratory flow;

measuring the expiratory flow through the meter.

15. A method according to claim 14, wherein the predetermined pressure is a pressure value preset for the meter.

16. A method according to claim 14, whereby the value of the predetermined pressure is decided automatically during use of the meter.

17. A method according to claim 14, whereby a release pressure value for the flow inhibiting means is preset for the meter, and the meter is programmed to provide a signal which operates the flow inhibition means at a pressure level lower than the release pressure value if said pressure level is maintained for a predetermined length of time.

18. A peak expiratory flow meter for determining the expiratory flow rate of a subject, comprising:

a flow passage having a first end for receiving expiratory air from a subject and a second end through which expiratory flow exits to the environment;

a closure operatively connected to said flow passage and normally effective to inhibit expiratory flow through said flow passage, said closure opening completely and in a short time relative to the duration of forced expiration from said subject in response to attainment of a predetermined expiratory pressure to allow expiratory flow through said flow passage and out through said second end to the environment.

* * * * *